US008859004B2

(12) United States Patent
Zhang et al.

(10) Patent No.: US 8,859,004 B2
(45) Date of Patent: Oct. 14, 2014

(54) PH-SENSITIVE NANOPARTICLES FOR ORAL INSULIN DELIVERY

(75) Inventors: Lijuan Zhang, Hong Kong (HK); Li Ling, Hong Kong (HK); Li Ying Zhou, Hong Kong (HK); Zhi Min Wu, Hong Kong (HK); Xin Dong Guo, Hong Kong (HK); Wei Jiang, Hong Kong (HK); Qian Luo, Hong Kong (HK); Yu Qian, Hong Kong (HK)

(73) Assignee: Nano and Advanced Materials Institute Limited, The Hong Kong University of Science and Technology, Clear Water Bay, Kowloon (HK)

( * ) Notice: Subject to any disclaimer, the term of this patent is extended or adjusted under 35 U.S.C. 154(b) by 152 days.

(21) Appl. No.: 13/561,106

(22) Filed: Jul. 30, 2012

(65) Prior Publication Data
US 2013/0034589 A1 Feb. 7, 2013

Related U.S. Application Data

(60) Provisional application No. 61/573,009, filed on Aug. 4, 2011.

(51) Int. Cl.
*A61K 9/51* (2006.01)
*A61K 38/28* (2006.01)
(52) U.S. Cl.
CPC .............. *A61K 9/5153* (2013.01); *A61K 38/28* (2013.01); *A61K 9/5161* (2013.01); *A61K 9/5192* (2013.01); *Y10S 977/906* (2013.01)
USPC ............................. 424/491; 977/906; 514/509
(58) Field of Classification Search
None
See application file for complete search history.

(56) References Cited

U.S. PATENT DOCUMENTS

| 7,871,988 | B1 | 1/2011 | Sung et al. | |
|---|---|---|---|---|
| 2007/0122486 | A1* | 5/2007 | McGurk et al. | 424/489 |
| 2007/0134332 | A1* | 6/2007 | Turnell et al. | 424/486 |
| 2008/0311182 | A1 | 12/2008 | Ferrari et al. | |
| 2010/0021549 | A1 | 1/2010 | Meyrueix et al. | |
| 2010/0310669 | A1* | 12/2010 | Paillard et al. | 424/497 |

FOREIGN PATENT DOCUMENTS

WO  WO2010113177 A2  10/2010

OTHER PUBLICATIONS

Li, et al., Preparation and Characterization of Insulin Nanoparticles Employing Chitosan and Poly(methylmethacrylate/methylmethacrylic acid) Copolymer, 6 J. Nanosci. Nanotech. 2874-86 (2006).*

Mundargi (Nano/micro technologies for delivering macromolecular therapeutics using poly(D,L-lactide-co-glycolide) and its derivatives, 125 J. Controlled Release 193 (2008).*
Mowiol® 4-88 (2013).*
Cui (Preparation of Insulin Loaded PLGA-Hp55 Nanoparticles for Oral Delivery, 96 J. Pharm. Sci. 421 (2007).*
Omathanu Pillai and Ramesh Panchagnula, "Insulin therapies—past, present and future", DDT vol. 6, No. 20 Oct. 2001.
Congrong Lin, Rajeev Gokhale, Jay S. Trivedi, and Vasant Ranade, "Recent Strategies and Methods for Improving Insulin Delivery", Drug Development Research 63:151-160 (2004).
Vikas Agarwal and Mansoor A. Khan, "Current Status of the Oral Delivery of Insulin", Pharmaceutical Technology Oct. 2001: 76-80.
Tin Wui Wong, "Design of oral insulin delivery systems", Journal of Drug Targeting, 2010; 18(2): 79-92.
Brian R. Stoll, Harry R. Leipold, Sam Milstein, David A. Edwards, "A mechanistic analysis of carrier-mediated oral delivery of protein therapeutics", Journal of Controlled Release 64 (2000) 217-228.
Susan K. Paulson, Margaret B. Vaughn, Susan M. Jessen, Yvette Lawal, Christopher J. Gresk, Bo Yan, Timothy J. Maziasz, Chyung S. Cook, and Aziz Karim, "Pharmacokinetics of Celecoxib after Oral Administration in Dogs and Humans: Effect of Food and Site of Absorption", JPET 297:638-645, 2001.
El-Sayed Khafagy, Mariko Morishita, Yoshinori Onuki, Kozo Takayama, "Current challenges in non-invasive insulin delivery systems: A comparative review", Advanced Drug Delivery Reviews 59 (2007) 1521-1546.
Harish Iyer, Anand Khedkar & Manish Verma, "Oral insulin—a review of current status", Diabetes, Obesity and Metabolism 12: 179-185, 2010.
Galindo-Rodriguez SA, Allemann E, Fessi H, Doelker E, "Polymeric nanoparticles for oral delivery of drugs and vaccines: a critical evaluation of in vivo studies", Crit Rev Ther Drug Carrier Syst. 2005; 22(5): 419-64.
Yunhui Wu, Alice Loper, Elizabeth Landis, Lisa Hettrick, Linda Novak, Kari Lynn, Cindy Chen, Karen Thompson, Ray Higghins, Udit Batra, Suhas Shelukar, Gloria Kwei, David Storye, "The role of biopharmaceutics in the development of a clinical nanoparticle formulation of MK-0869: a Beagle dog model predicts improved bioavailability and diminshed food effect on absorption in human", International Journal of Pharmaceutics 285 (2004) 135-146.
Filippos Kesisoglou, Santipharp Panmai, Yunhui Wu, "Nanosizing— Oral formulation development and biopharmaceutical evaluation", Advanced Drug Delivery Reviews 59 (2007) 631-644.
Christiane Damgé, Catarina Pinto Reis & Philippe Maincent, "Nanoparticle strategies for the oral delivery of insulin", Expert Opin. Drug Deliv. (2008) 5(1): 45-68.

(Continued)

*Primary Examiner* — H. Sarah Park
(74) *Attorney, Agent, or Firm* — Ella Cheong Hong Kong; Sam T. Yip

(57) ABSTRACT

The present invention discloses the pH-sensitive nanoparticles composed of pH-sensitive polymer, hydrophobic material, internal stabilizer, external stabilizer content and insulin drug. The present invention also includes a method for preparation of pH-sensitive nanoparticles, in particular, a multiple emulsions solvent evaporation method. The pH-sensitive nanoparticles of the present invention show good pH-sensitive property with 100-300 nanometer particle size. Significant decrease in blood glucose level is observed in streptozotocin (STZ)-induced diabetic rats and the bioavailability of insulin is more than 10% after oral administration of the insulin-loaded pH-sensitive nanoparticles.

16 Claims, 5 Drawing Sheets

(56) References Cited

OTHER PUBLICATIONS

Camile B. Woitiski, Rui A. Carvalho, Ant' onio J. Ribeiro, Ronald J. Neufeld and Francisco Veiga, "Strategies Toward the Improved Oral Delivery of Insulin Nanoparticles via Gastrointestinal Uptake and Translocation", Biodrugs 2008; 22 (4): 223-237.

Anne des Rieux, Virginie Fievez, Marie Garinot, Yves-Jacques Schneider, Véronique Preéat, "Nanoparticles as potential oral delivery systems of proteins and vaccines: A mechanistic approach", Journal of Controlled Release 116 (2006) 1-27.

11th International Congress on Amino Acids, Peptides and Proteins, Vienna, Austria, Aug. 3-7, 2009.

Yu-Hsin Lin, Kiran Sonaje, Kurt M. Lin, Jyuhn-Huarng Juang, Fwu-Long Mi, Han-Wen Yang, Hsing-Wen Sung, "Multi-ion-crosslinked nanoparticles with pH-responsive characteristics for oral delivery of protein drugs", Journal of Controlled Release 132 (2008) 141-149.

Fu-De Cui, An-Jin Tao, Dong-Mei Cun, Li-Qiang Zhang, Kai Shi, "Preparation of Insulin Loaded PPGA-Hp55 Nanoparticles for Oral Delivery", Journal of Pharmaceutical Sciences, vol. 96, No. 2:421-427, Feb. 2007.

S. Sajeesh, Chandra P. Sharma, "Novel pH Responsive Polymethacrylic Acid—Chitosan—Polyethylene Glycol Nanoparticles for Oral Peptide Delivery", J Biomed Mater Res B Appl Biomater. Feb. 2006;76(2):298-305.

Catarina Pinto Reisa, Ant' onio J. Ribeiro, Simone Houng, Francisco Veiga, Ronald J. Neufeld, "Nanoparticulate delivery system for insulin: Design, characterization and in vitro/in vivo bioactivity", European Journal of Pharmaceutical Sciences 30 (2007) 392-397.

Kiran Sonaje, Yu-Hsin Lin, Jyuhn-Huarng Juang, Shiaw-Pyng Wey, Chiung-Tong Chen, Hsing-Wen Sung, "In vivo evaluation of safety and efficacy of self-assembled nanoparticles for oral insulin delivery", Biomaterials 30 (2009) 2329-2339.

Lichen Yin, Jieying Ding, Chunbai He, Liming Cui, Cui Tang, Chunhua Yin, "Drug permeability and mucoadhesion properties of thiolated trimethyl chitosan nanoparticles in oral insulin delivery", Biomaterials 29 (2009) 5691-700.

Anchalee Jintapattanakit, Varaporn Buraphacheep Junyaprasert, Thomas Kissel, "The Role of Mucoadhesion of Trimethyl Chitosan and PEGylated Trimethyl Chitosan Nanocomplexes in Insulin Uptake", Journal of Pharmaceutical Sciences, vol. 98, No. 12:4818-4830, Dec. 2009.

Britta Deutel, Melanie Greindl, Michael Thaurer, and Andreas Bernkop-SchnOrch, "Novel Insulin Thiomer Nanoparticles: In Vivo Evaluation of an Oral Drug Delivery System", Biomacromolecules 2008,9,278-285.

Anchalee Jintapattanakit, Varaporn B. Junyaprasert, Shirui Maob, Johannes Sitterberg, Udo Bakowsky, Thomas Kissel, "Peroral delivery of insulin using chitosan derivatives: A comparative study of polyelectrolyte nanocomplexes and nanoparticles", International Journal of Pharmaceutics 342 (2007) 240-249.

Kiran Sonaje, Kun-Ju Lin, Shiaw-Pyng Wey, Che-Kuan Lin, Tzyy-Harn Yeh, Ho-Ngoc Nguyen, Chia-Wei Hsu, Tzu-Chen Yen, Jyuhn-Huarng Juang, Hsing-Wen Sung, "Biodistribution, pharmacodynamics and pharmacokinetics of insulin analogues in a rat model: Oral delivery using pH-Responsive nanoparticles vs. subcutaneous injection", Biomaterials 26 (2010) 6849-58.

Kiran Sonaje, Yi-Jia Chen, Hsin-Lung Chen, Shiaw-Pyng Wey, Jyuhn-Huarng Juang, Ho-Ngoc Nguyen, Chia-Wei Hsu, Kun-Ju Lin, Hsing-Wen Sung, "Enteric-coated capsules filled with freeze-dried chitosan/poly(g-glutamic acid) nanoparticles for oral insulin delivery", Biomaterials 31 (2010) 3384-3394.

Andreas Bernkop-Schnürch, "Chitosan and its derivatives: potential excipients for peroral peptide delivery systems", International Journal of Pharmaceutics 194 (2000) 1-13.

Yu-Hsin Lin, Chiung-Tong Chen, Hsiang-Fa Liang, Anandrao R Kulkarni, Po-Wei Lee, Chun-Hung Chen and Hsing-Wen Sung, "Novel nanoparticles for oral insulin delivery via the paracellular pathway", Nanotechnology 18 (2007) 105102.

Mauro Ferrari, "Nanovector therapeutics", Current Opinion in Chemical Biology 2005, 9:343-346.

Cliff Wong, Triantafyllos Stylianopoulos, Jian Cui, John Martin, Vikash P. Chauhan, Wen Jiang, Zoran Popovic, Rakesh K. Jain, Moungi G. Bawendi, and Dai Fukumura, "Multistage nanoparticle delivery system for deep penetration into tumor tissue", Proc Natl Acad Sci U S A. Feb. 8, 2011;108(6):2426-31.

Rita E. Serda, Biana Godin, Elvin Blanco, Ciro Chiappini, Mauro Ferrari, "Multi-stage delivery nano-particle systems for therapeutic applications", Biochimica et Biophysica Acta 1810 (2011) 317-329.

Ennio Tasciotti, Xuewu Liu, Rohan Bhavane, Kevin Plant, Ashley D. Leonard, B. Katherine Price, Mark Ming-Cheng Cheng, Paolo Decuzzi, James M. Tour, Fredika Robertson and Mauro Ferrari, "Mesoporous silicon particles as a multistage delivery system for imaging and therapeutic applications", Nat Nanotechnol. Mar. 2008;3(3):151-7.

* cited by examiner

US 8,859,004 B2

PH-SENSITIVE NANOPARTICLES FOR ORAL INSULIN DELIVERY

CROSS-REFERENCE TO RELATED APPLICATIONS

The present application claims priority of U.S. provisional application Ser. No. 61/573,009 filed Aug. 4, 2011, the disclosure of which is incorporated herein by reference.

FIELD OF THE INVENTION

This invention relates to nanoparticles and methods of preparing the same which are useful in the biopharmaceutical technology area, in particular, to pH-sensitive nanoparticles and their preparation methods.

TECHNICAL BACKGROUND

Diabetes is characterized by chronic high blood glucose levels. There were about 250 million diabetes patients all around the world as of 2007, especially in undeveloped and developing countries. It is estimated that there will be 380 million patients by 2025. Therefore, diabetes is a critical global problem.

Insulin is delivered in liquid injection form for diabetes treatment because of its short half-life and degradation in the gastrointestinal track. It must be given to the patients frequently, which brings great inconvenience and economic burden. There is a great demand for the development of a more convenient non-injection form for insulin. An oral dosage form has been widely studied. Insulin pH-sensitive nanoparticles can control insulin release and improve its oral bioavailability.

PCT publication WO2010113177-A2 discloses an oral insulin pH-sensitive agent comprising insulin and Eudragit L100. The agent shows a good pH-sensitive property when the particle size is 40 μm; however this size is not suitable for insulin absorption. Further, the disclosed preparation technique has some limitations since the required double emulsion of an agent comprising liquid paraffin is unstable and the evaporation of the solvent is slow.

Patent application publication US2010021549-A1 provides a core-shell particle comprising insulin and pH-sensitive polymers. The pH-sensitive polymers are HPMCP and HPMCAS. The release of insulin from the particle is slow in an acidic medium while fast in a neutral medium. The particle is prepared by a fluidized bed spraying technique with 2 mm particle size.

Paper (J Pharm Sci-US, 2007, 96, 421) describes an oral insulin pH-sensitive nanoparticle composed of HP55 and PLGA. The nanoparticles are prepared by a solvent evaporation method. In this method, both polymers and insulin are dissolved into a solvent containing water, which has some limitations. Although phase separation is easily generated when the concentration is high, the process suffers from low encapsulation efficiency. Further, although insulin easily diffuses outwards, a lower pH-sensitive property is a result.

HP55 is a pH-sensitive cellulose coating designed for use in enteric coating materials. HP55 can withstand prolonged contact with an acidic gastric environment, but readily dissolves in the mildly acidic to neutral fluid of the small intestine. HP55, when used to prepare insulin-loaded nanoparticles, is able to reduce insulin release in the stomach and thus increase the bioavailability.

However, there is still a need for orally-deliverable insulin particles having increased bioavailability and a need for processes that produce a high yield of such insulin particles.

SUMMARY OF THE INVENTION

It is one object of the present invention to provide novel and effective pH-sensitive nanoparticles for oral insulin delivery using a modified double emulsion solvent evaporation method (also called multiple emulsions solvent evaporation method). The insulin-loaded nanoparticles are sensitive to pH changes, and as such, can dissolve rapidly in the upper region of the small intestine and release insulin. The pH-sensitive nanoparticles are configured to control insulin release and improve its oral bioavailability. By mixing two different solvents with dissolved polymers, a pH-sensitive polymer and a biodegradable polymer, and by using an insulin solution and a polyvinyl alcohol (PVA) solution, a double emulsion can be formed by ultrasonic emulsification, and evaporation of the solvents causes the final formation of pH-sensitive nanoparticles. The pH-sensitive nanoparticles prepared by the multiple emulsions solvent evaporation method of the present invention are found to increase the bioavailability of the insulin as compared to the particles prepared by the conventional single emulsion solvent diffusion method.

The method of the present invention increase a step characteristic of the prior art, that is, creating nanoparticles by the double emulsion. The double emulsion formation step can encapsulate a hydrophilic drug and can rapidly evaporate solvent to form nanoparticles. The invention has the advantage that it can completely release insulin from the pH-sensitive nanoparticles compared to the prior art. It also has the advantage of avoiding low encapsulation efficiency. Only about 65% of encapsulation efficiency is provided in the prior art, while the encapsulation efficiency using the method of the present invention can be up to 95%. The invention provides the additional advantage that it produces better pH-sensitive release of insulin than the prior art.

According to one aspect of the invention, a method for encapsulating insulin to form pH-sensitive nanoparticles is provided, which comprises forming an inner water phase comprising an insulin solution at a concentration range of 5 to 10 mg/mL; forming an oil phase comprising a dichloromethane/acetone solution of HP55 and poly(lactic acid-co-glycolic acid) (PLGA) at a concentration range of 20 to 50 mg/mL; forming an external aqueous phase comprising a PVA solution as a stabilizer at a concentration range of 1 to 10 mg/mL; forming an initial emulsion comprising the inner water phase at a volume of 0.5 to 1 mL and the oil phase at a volume of 3 to 5 mL, wherein the initial emulsion is formed by ultrasonic emulsification for a time range of 30 to 60 s at a power range of 40 to 60 w; forming a double emulsion comprising the initial emulsion at a volume of 3.5 to 6 mL and the external aqueous phase at a volume of 20 to 40 mL, wherein the double emulsion is formed by ultrasonic for a time range of 60 to 120 s at a power range of 40 to 60 w; forming an insulin-loaded PLGA/HP55 nanoparticles by evaporation of the dichloromethane/acetone from the double emulsion; forming a purified insulin-loaded PLGA/HP55 nanoparticles by centrifugation and water washing of the PLGA/HP55 nanoparticles for three times; forming the pH-sensitive nanoparticles which are cationic by freeze-drying the purified insulin-loaded PLGA/HP55 nanoparticles.

According to another aspect of the invention, pH-sensitive nanoparticles are provided. The nanoparticles are produced by the methods described herein. The methods of the invention result in products that have better physical characteristics, bioavailability and bioactivity than nanoparticles formed according to prior art methods. The pH-sensitive polymer of the nanoparticles is hydroxypropylmethylcellulose phthalate (HPMCP) selected from the group consisting of HP50 and HP55. In an exemplary embodiment, HP55 is used as the pH-sensitive polymer for preparing the nanoparticles of the present invention. In addition, each of the nanoparticles prepared by the methods further includes a hydrophobic polymer which is also polycationic. The hydrophobic polymer used in the present invention can be any polycationic polymer with quaternary ammonium cations such as Eurdragit RS polymer having quaternary ammonium cations.

DEFINITION

I. Insulin

Figure 1:
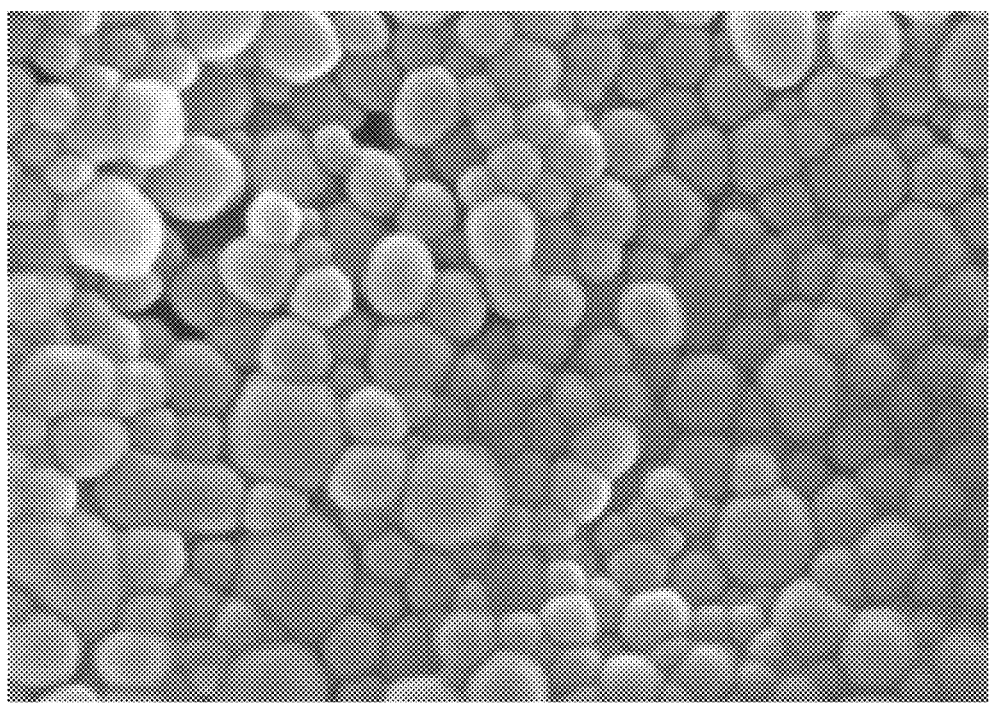
FIG. 1 shows the SEM image of the insulin-loaded PLGA/HP55 nanoparticles.

The term "insulin", as used herein, refers to any naturally occurring or recombinant insulin. Accordingly, insulin for use in the invention includes, for example, insulin analogs and derivatives. Insulin from any suitable species can be used, such as human, pig, cow, dog, sheep. In a preferred embodiment, the insulin is porcine insulin. "Regular insulin" as disclosed herein may refer to naturally-occurring insulin or synthetic insulin molecule. Naturally-occurring insulin or synthetic insulin molecule may include, but not limited to, monomeric, polymeric and/or fibril-like insulin, and different forms of insulin molecule depends on different pH values.

Porcine Insulin is a two chain, glycosylated polypeptide chain containing 51 amino acids and having a molecular mass of 5,777 Dalton. The alpha and beta chains are joined by two interchain disulfide bonds. The alpha chain contains an intra-chain disulfide bond. Insulin regulates the cellular uptake, utilization, and storage of glucose, amino acids, and fatty acids and inhibits the breakdown of glycogen, protein, and fat. Insulin having various degrees of biological activity is commercially available. For instance, it is possible to purchase low-, intermediate-, and rapid-acting forms of insulin. In a preferred embodiment, the biological activity range of porcine insulin is 27 to 28 IU/mg.

II. The pH-Sensitive Nanoparticles

As used herein, pH-sensitive nanoparticles refer to nanoparticles having stability in a gastric acid environment and releasing insulin in the intestinal environment. The pH-sensitive nanoparticles comprise a pH-sensitive polymer, which is typically HP55. HP55 is widely used as an enteric coating polymer in the pharmaceutical industry. It has a high content (31%) of phthalate groups. HP55 cannot be directly dissolved in the dichloromethane, which is the main reason that the HP55-based nanoparticles cannot be produced using the traditional multiple emulsions solvent evaporation method.

The HP-55 based nanoparticles for use in the invention can be made by the modified multiple emulsions solvent evaporation method, using the mixture of dichloromethane and acetone as the solvent to dissolve the HP55 and other polymers.

DETAILED DESCRIPTION OF THE INVENTION

Example 1

Preparation of Insulin-Loaded PLGA/HP55 Nanoparticles

HP55 as a pH-sensitive material/polymer is used to prepare PLGA/HP55 nanoparticles by two different methodologies. Methodology A: HP55 is dissolved in an organic phase of acetone and alcohol to form a mixture, the mixture is used as the coating of PLGA nanoparticles to form PLGA/HP55 nanoparticles. Methodology B: Both PLGA and HP55 are dissolved in an organic phase of dichloromethane and acetone to form a mixture which is directly used to form PLGA/HP55 nanoparticles.

TABLE 1

| Way of adding HP55 | Methodology A | Methodology B |
| --- | --- | --- |
| particle size, nm | 303.8 ± 25.4 | 181.9 ± 19.0 |
| encapsulation efficiency, % | 74.54 ± 1.01 | 94.25 ± 1.24 |

As shown in Table 1, the encapsulation efficiency of nanoparticles by Methodology B is higher than that by Methodology A. The reasons for lower encapsulation efficiency by Methodology A are: (i) insulin easily spreads into an external water phase during long periods of magnetic stirring, and (ii) part of HP55 is dissolved in water washing, skiving the protective layer for the insulin. Furthermore, nanoparticles prepared by Methodology A are out of shape. Some particles form aggregations. In contrast, nanoparticles prepared by Methodology B are spherical in shape with smaller particle size. Thus, Methodology B is a preferred embodiment to prepare insulin-loaded PLGA/HP55 nanoparticles.

The insulin-loaded PLGA/HP55 nanoparticles are prepared as follows: Insulin (5 mg) is dissolved into 0.1% PVA (1.0 mL, pH=2) or glycerin as an internal stabilizer to form internal water phase (W1), poly (lactic acid-co-glycolic acid) (PLGA) (100 mg) and HP55 (50 mg) are dissolved into 5 mL of an organic solvent (volume ratio of dichloromethane and acetone is 4:1 or 3:1) to form an oil phase (O), respectively. Optionally, a hydrophobic carrier is added to the oil phase (O) before pouring W1 into O. At 25° C., 1 mL W1 is poured into O, and the mixture is ultrasonic for 0.5 min at 60 W to obtain an initial W1/O emulsion. The initial emulsion is poured into an external water phase with 1.0% PVA (10 mL) (W2) quickly, and the mixture is ultrasonic for 4 min at 60 W to obtain a double W1/O/W2 emulsion. The acetone and dichloromethane in the double emulsion are eliminated totally by rotary evaporation (45° C., 451 mbar, 15 min). The residue is centrifuged (10° C., 20,000 rpm, 10 min). Finally, the pH-sensitive nanoparticles are obtained from the precipitate after at least twice of washing by distilled water and freeze drying.

The molecular weight of the PVA used in the present invention is from 31,000 to 50,000 daltons. The molecular weight of the hydrophobic polymer or carrier used in the present invention is from 20,000 to 40,000 daltons.

Example 2

Characterization of Insulin-Loaded PLGA/HP55 Nanoparticles

The morphological examination of the insulin-loaded PLGA/HP55 nanoparticles is performed by studying their SEM image as shown in FIG. 1. The product is white fine powder. The prepared PLGA/HP55 nanoparticles from Methodology B in Example 1 have a mean particles size 181.9±19.0 nm with a PDI 0.093±0.031. The insulin loading efficiency is 90.85±1.09% (not determined from FIG. 1). The insulin-loaded PLGA/HP55 nanoparticles prepared by the multiple emulsions solvent evaporation method, that is the double emulsion used in the method of the present invention, have a high drug loading, high encapsulation efficiency and small size.

Example 3

In Vitro Insulin Release Study

Figure 2:
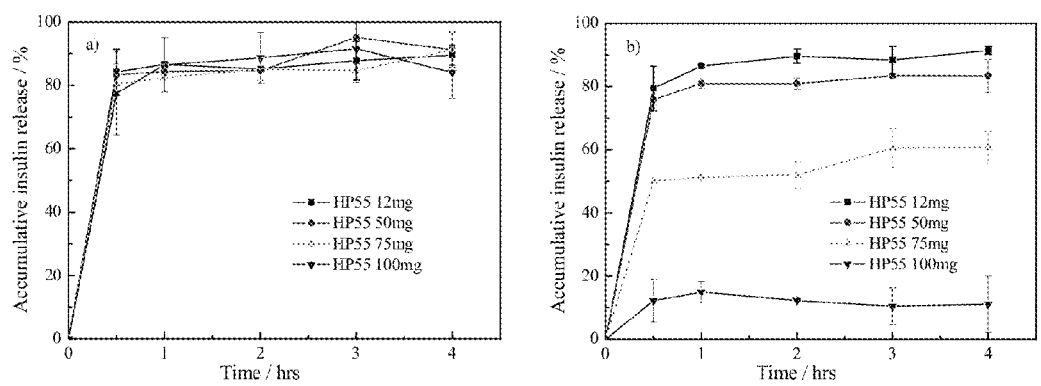
FIG. 2 shows the in vitro release properties of insulin from nanoparticles at different HP55 amount in the pH=7.4 PBS (left panel) and pH=1.2 HCl (right panel).

The amount of HP55 coated on the PLGA/HP55 nanoparticles would affect the pH-sensitivity of the PLGA/HP55 nanoparticles. Thus, the effect of different amounts of HP55 in the pH-sensitivity of the PLGA/HP55 nanoparticles is determined by an in vitro insulin release study. The effect of different amount of HP55 on the release properties of insulin is evaluated in a simulated gastrointestinal fluid. FIG. 2 shows the in vitro release rate of insulin from nanoparticles at different HP55 amounts in solutions having pH=7.4 PBS (a) and pH=1.2 HCl (b), respectively.

PLGA/HP55 nanoparticles with different amounts of HP55 release more than 75% insulin in pH=7.4 PBS. When both PLGA and HP55 are dissolved in an organic solvent to entrap insulin, the interaction between HP55 and insulin is stronger than that between PLGA and insulin; most insulin molecules tend to disperse in HP55 rather than in PLGA. In pH=7.4 PBS, the carboxyl group (—COOH) of HP55 loses a proton to become COO⁻ in order to increase its solubility and promote insulin release. The pH responsivity increases and less insulin releases with the increase in HP55 amount in pH=1.2 HCl. When the amount of HP55 reaches 100 mg, only 20% insulin is released from PLGA/HP55 nanoparticles. However, when the amount of HP55 is above 100 mg, white precipitates are formed.

Figure 3:
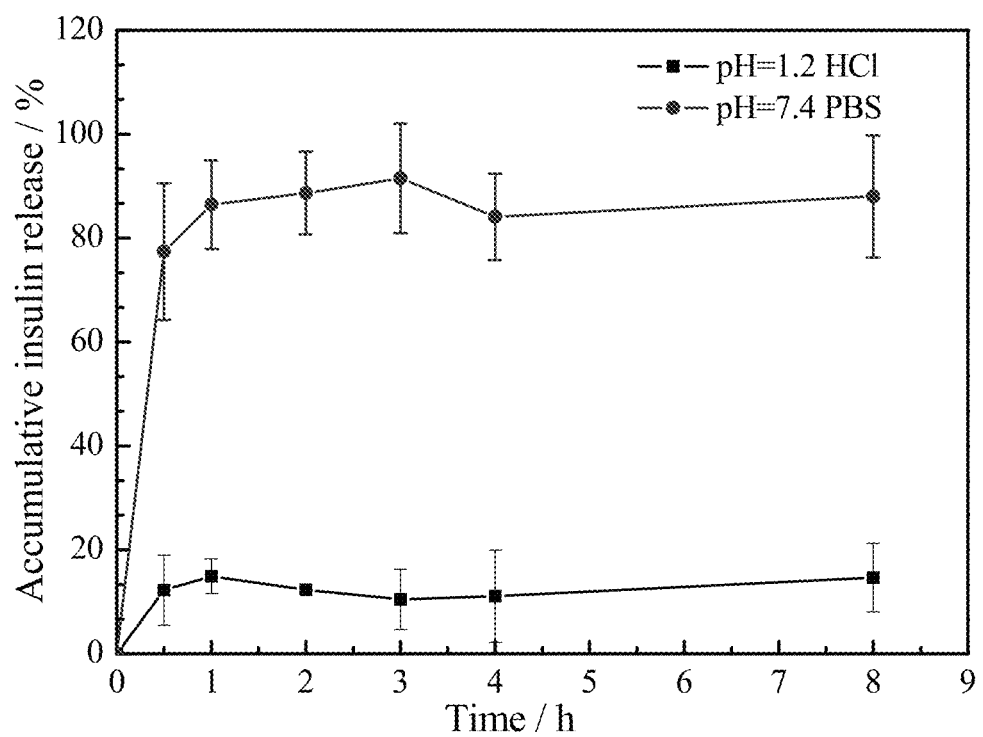
FIG. 3 shows a representative in vitro study with insulin drug release profile of pH-sensitive nanoparticles in the simulated gastrointestinal mediums.

FIG. 3 shows a representative protein drug (for example, insulin) release profile in a pH-sensitive study with an exemplary composition including 50 mg of PLGA, 100 mg of HP55, and 10 mg of insulin molecules for preparation of the pH-sensitive nanoparticles of the present invention.

Example 4

Figure 4:
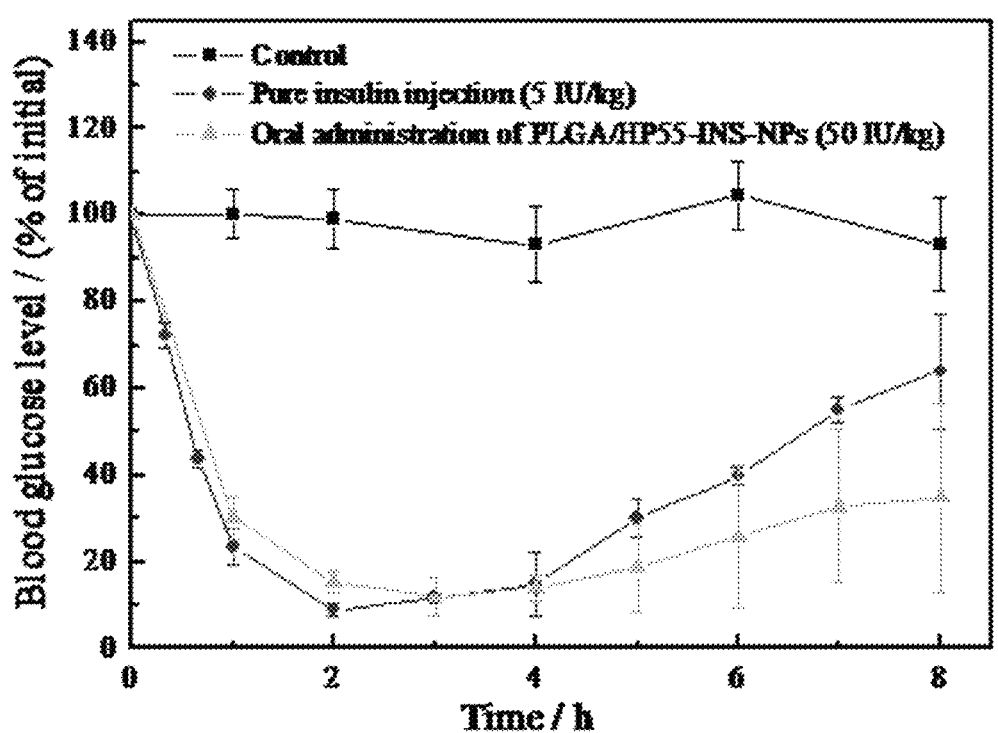
FIG. 4 shows the blood glucose level versus time profiles after oral administration of insulin-load pH-sensitive nanoparticles or subcutaneous administration of insulin solution to the disease model.
Figure 5:
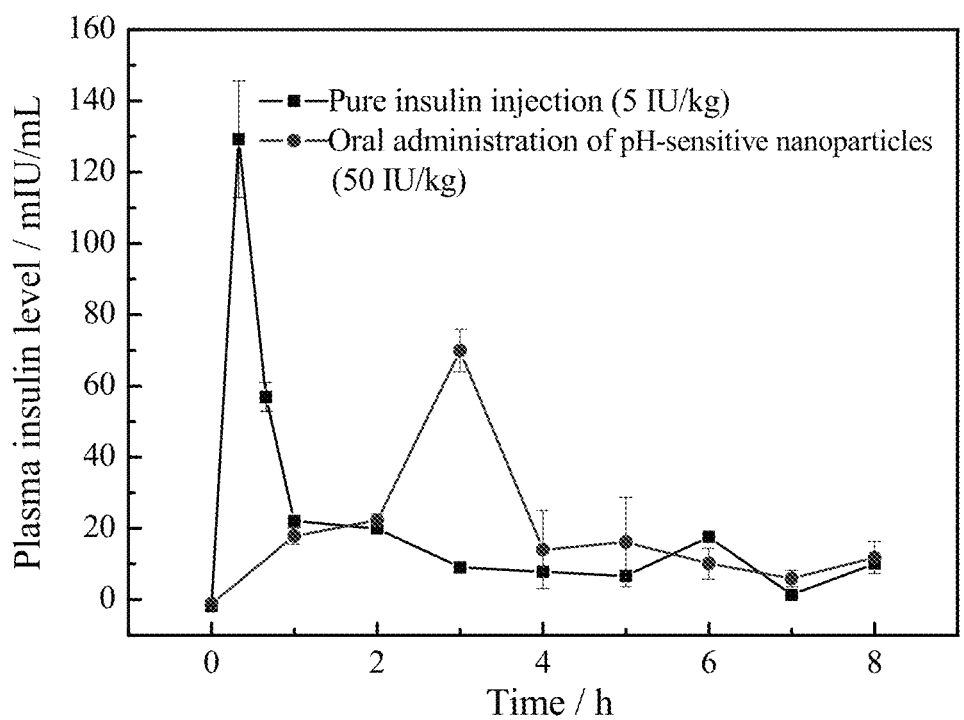
FIG. 5 shows the serum insulin level versus time profiles after oral administration of insulin-load pH-sensitive nanoparticles or subcutaneous administration of insulin solution to the disease model.

In Vivo Study with Insulin-Loaded PLGA/HP55 Nanoparticles After Oral Administration in Diabetic Rats Insulin-loaded PLGA/HP55 nanoparticles (50 IU/kg) are orally administrated to diabetic rats. Pure insulin solution (5 IU/kg) is subcutaneously injected (SC) to the diabetic rats as the positive control. Blood samples are collected from the tip of the tail vein of the treated rats at predetermined time points. The hypoglycemic effects are demonstrated by the percentage change of the blood glucose level from the initial value. FIG. 4 shows the hypoglycemic effects of pure insulin solution and the insulin-loaded PLGA/HP55 nanoparticles. The concentrations of insulin in serum samples are calculated as a function of time, shown in FIG. 5. The pharmacokinetic parameters for plasma insulin levels after oral insulin-loaded PLGA/HP55 nanoparticles are shown in Table 2.

HP55 protects the nanoparticles of the present invention from being damaged in the stomach tract by acid and/or enzymes. When the nanoparticles arrive at the intestinal tract, HP55/PLGA nanoparticles swell and release insulin quickly, resulting in a significant hypoglycemic effect. About 70% blood glucose level decreases in 1 h with a sustained hypoglycemic effect over 6 hours.

TABLE 2

| Samples | $T_{max}$/hrs | $C_{max}$/(μIU/mL) | AUC | $BA_R$/% |
|---|---|---|---|---|
| Pure insulin injection (5 IU/kg) | 0.33 | 129.21 | 143.76 | 100 |
| Oral PLGA/HP55 nanoparticles feeding (50 IU/kg) | 3 | 69.93 | 161.69 | 11.25 |

As shown in Table 2, the diabetic rats subcutaneously treated with the pure insulin injection show a maximum plasma concentration at about 0.33 hour after the injection, whereas those with oral administration of the insulin-loaded PLGA/HP55 nanoparticles of the present invention show a maximum plasma concentration at about 3 hours after treatment. The $C_{max}$ of those with oral administration of the insulin-loaded PLGA/HP55 nanoparticles is 69.93 μIU/mL; $AUC_{(0-10\,h)}$ is 161.69 which corresponds to a $BA_R$ of 11.25%.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims.

What we claim:

1. A method of preparing pH-sensitive insulin-loaded nanoparticles comprising:
   (a) mixing one part of insulin and two parts of an internal stabilizer to form solution A which is an internal water phase (W1);
   (b) dissolving one part of hydrophobic polymer with a molecular weight from 20,000 to 40,000 daltons and two parts of pH-sensitive polymer in a solvent of dichloromethane and acetone with a volume ratio of 4:1 to 3:1 to form solution B which is an oil phase (O);
   (c) forming solution C which is an external phase (W2) comprising an external aqueous stabilizer with a molecular weight from 31,000 to 50,000 daltons;

(d) forming an initial emulsion (W1/O) comprising solution A obtained from (a) and solution B obtained from (b) by first ultrasonic emulsification;

(e) forming a double emulsion (W1/O/W2) comprising the initial emulsion obtained from (d) and the external aqueous stabilizer of solution C obtained from (c) by second ultrasonic emulsification;

(f) forming the pH-sensitive insulin-loaded nanoparticles by evaporation of the solvent, water washing, centrifugation of the nanoparticles, and freeze drying.

2. The method of claim 1, wherein said internal stabilizer is a solution of 0.1% polyvinyl alcohol which is mixed with said insulin at pH 2.

3. The method of claim 1, wherein said hydrophobic polymer is poly (lactic acid-co-glycolic acid) and said pH-sensitive polymer is HP50 or HP55.

4. The method of claim 1, wherein 0.5-1 mL of said solution A is poured into 3-5 mL of said solution B to form a first mixture, and the first mixture is then immediately subjected to said first ultrasonic emulsification at power of 40-60 W for 30-60 seconds to form said initial emulsion.

5. The method of claim 1, wherein said double emulsion is formed by mixing 3.5-6 mL of said initial emulsion and 20-40 mL of said solution C to form a second mixture, and the second mixture is then subject to said second ultrasonic emulsification at power of 40-60 W for 60-120 seconds to form said double emulsion.

6. The method of claim 1, wherein said pH-sensitive insulin-loaded nanoparticles are formed by evaporating said solvent from said double emulsion at 45° C. and at 451 mbar for 15 minutes and centrifuging at 10° C. and at 20,000 rpm for 10 minutes to obtain a residue, the residue is then precipitated by said water washing for at least twice followed by said freeze-drying.

7. The method of claim 1, wherein the nanoparticles have a mean particle size of about 100-300 nanometers.

8. The method of claim 2, wherein the amount of said insulin is about 5 mg while the volume of said 0.1% polyvinyl alcohol solution is about 10 mL.

9. The method of claim 3, wherein the amount of said poly (lactic acid-co-glycolic acid) is about 50 mg while the amount of HP50 or HP55 is 100 mg.

10. A pH-sensitive nanoparticle for oral administration prepared by the method of claim 1.

11. An oral composition configured to deliver insulin to a subject in needs thereof in a controlled release manner through gastrointestinal tract comprising a plurality of said pH-sensitive nanoparticles of claim 10.

12. A pharmaceutically acceptable carrier comprising one or more of said pH-sensitive nanoparticles of claim 10.

13. The method of claim 1, wherein the hydrophobic polymer is selected from the group consisting of poly lactic acid, poly(lactic acid-co-glycolic acid) (ratio of lactic acid:glycolic acid=85:15), poly(lactic acid-co-glycolic acid) (ratio of lactic acid:glycolic acid=75:25), and poly(lactic acid-co-glycolic acid) (ratio of lactic acid:glycolic acid=50:50).

14. The method of claim 1, wherein the pH-sensitive polymer is HPMCP selected from the group consisting of HP50 and HP55.

15. The method of claim 1, wherein the pH-sensitive polymer is HP55.

16. The method of claim 1, wherein the internal stabilizer is selected from the group consisting of glycerin and polyvinyl alcohol; wherein the external aqueous stabilizer is polyvinyl alcohol.

* * * * *